United States Patent
Mahashabde et al.

(10) Patent No.: US 6,436,378 B1
(45) Date of Patent: Aug. 20, 2002

(54) COMPOSITION

(75) Inventors: Chhaya Shirish Mahashabde; Sunil Shyamsunder Agrawal, both of Mumbai (IN)

(73) Assignee: Colgate-Palmolive Company, New York, NY (US)

(*) Notice: Subject to any disclaimer, the term of this patent is extended or adjusted under 35 U.S.C. 154(b) by 0 days.

(21) Appl. No.: 09/795,898

(22) Filed: Feb. 28, 2001

(51) Int. Cl.$^7$ .............. A61K 7/42; A61K 7/44; A61K 7/00; A61K 31/44; A61K 31/34
(52) U.S. Cl. .......... 424/59; 424/60; 424/401; 514/356; 514/474; 514/783
(58) Field of Search .............. 424/401, 59, 60, 424/62, 356, 474, 783

(56) References Cited

U.S. PATENT DOCUMENTS

| | | | | |
|---|---|---|---|---|
| 4,096,240 A | * | 6/1978 | Mathur | 424/59 |
| 4,136,166 A | * | 1/1979 | Barnett et al. | 424/62 |
| 5,545,399 A | * | 8/1996 | Lee et al. | 424/59 |
| 5,766,575 A | * | 6/1998 | Crotty et al. | 424/59 |
| 5,767,158 A | * | 6/1998 | Suetsugu et al. | 514/563 |
| 5,858,997 A | * | 1/1999 | Crotty et al. | 514/159 |
| 5,958,437 A | * | 9/1999 | Zaveri | 424/401 |
| 6,203,781 B1 | * | 3/2001 | Chevalier et al. | 424/63 |

FOREIGN PATENT DOCUMENTS

WO  WO-94/09756 A1  *  5/1994

* cited by examiner

*Primary Examiner*—Jose G. Dees
*Assistant Examiner*—Marina Lamm
(74) *Attorney, Agent, or Firm*—Martin B. Barancik

(57) ABSTRACT

A composition comprising a cream or lotion base said base further comprising
a. An active agent or mixture thereof which brings about skin lightening, and
b. An active agent or mixture thereof which prevents skin from further darkening when exposed to ultraviolet light.

5 Claims, No Drawings

COMPOSITION

BACKGROUND OF THE INVENTION

Various formulations are now being employed to bring about desirable visible skin effects. Among these desirable effects are skin lightening, particularly in Asia wherein a light skin is considered to be an element of beauty.

In order to achieve this goal, "leave-on" formulations such as creams and lotions have now been invented with various active agents. Among these agents are materials which inhibit the synthesis of melanin, and can bring about skin lightening, materials which prevent skin from further darkening by induced melanogenesis by ultraviolet rays, generally UV inhibitors (sunscreens) and the further use of materials which assist in maintaining youthful skin.

SUMMARY OF INVENTION

In accordance with the invention, there is a composition comprising a cream or lotion base which further comprises an active agent or mixture thereof which brings about skin lightening and a further active agent or mixture thereof which prevents skin from further darkening. Each of the active agents or mixture thereof are present in quantities in the formulation which bring about skin lightening and prevent further skin darkening.

A further component of the formulation can be an amount of an antioxidant which assists in maintaining youthful skin.

A still further component can be an inorganic sunscreen such as titanium dioxide or zinc oxide. These materials are employed to obtain a rapid onset of perceivable whitening effect.

DETAILED DESCRIPTION OF THE INVENTION

Examples of skin lightening compounds include hydroquinone, arbutin, Kojic acid, and ascorbic acid. Among these materials are those which can inhibit the synthesis of melanin, a compound within skin which darkens it. Examples of such compounds include tyrosinase inhibitors, for example herbal extracts from aspergillus, songyi, licorice, and bearberry. Other agents are niacinamide, sodium ascorbyl phosphate, herbal extract complex of scutelleria, saxifrage, grape mulberry (Biowhite) and a Gatuline complex containing herbal extract complex of licorice and aspergillus ferment. Of these, it is preferred to use herbal extracts from scutelleria, saxifrage, grape and mulberry marketed as "Biowhite" available from Coletica and a combination of niacinamide and a Gatuline complex (herbal extract complex of aspergillus ferment and licorice extract) and sodium ascorbyl phosphate (SAP).

The second group is materials which prevent further darkening to the skin, generally occurring through induced melanogenesis by UV rays. Various known UV inhibitors can accomplish this protection, desirably over both the range of electromagnetic spectrum designated as UVB and UVA. Examples of UV inhibitors include families such as salicylates, cinnamic acid derivatives, para amino benzoic acid and specific agents either alone or in combination such as octyl methoxycinnamate (OMC), benzophenone-3, methylene bis-benzotriazolyl tetramethyl butyl phenol, and the like. Preferred sunscreen UV inhibitors are a combination of Octyl Methoxy Cinnamate with benzophenone-3 and Octyl methoxycinnamate with methylene bis-benzotriazolyl tetramethyl butyl phenol.

Inorganic sunscreen actives may also be used such as microfine titanium dioxide or zinc oxide. Amounts of the sunscreen agents (whether organic or inorganic) will generally range from 0.1–20%, preferably from 0.1 to 15%, desirably about 0.1 to about 5 or about 3 wt. % of the composition.

Agents which assist in maintaining youthful skin are generally known antioxidants such as the vitamins, particularly vitamins E, A and C and their precursor derivatives which are converted to the active vitamin by skin systems.

More than one vitamin, a vitamin and a precursor, or precursor can be present in the composition. Examples of precursors are esters of Vitamins A and E, such as esters having one to about twenty carbon atoms. Examples of effective esters are those having about 1 to about 20 carbon atoms, for example, the methyl, propyl, hexyl, decyl, lauryl, palmityl and behenyl ester of the vitamin such as the methyl ester of Vitamin E or the palmitate ester of Vitamin A. Of the actual vitamin the alpha tocopherol compound is preferred as Vitamin E. Similar precursors can be used for Vitamin C. Other precursors are cholesteryl Vitamin C, sodium ascorbyl phosphate and the like. Retinyl palmitate is the preferred precursor for Vitamin A. Vitamin E methyl ester (Vitamin E acetate) is the preferred precursor for Vitamin E.

Various leave-on bases can be employed such as lotions and creams. Moisturizing or vanishing bases can be employed. Virtually any lotion or cream bases can be employed. The most desirable ones are those which are compatible with the above active agents while maintaining an ease of spreading and good skin feel including a lack of greasiness. A preferred base foundation is comprised of a long chain alkyl carboxylic acid having from about 10 to about 20 carbon atoms, desirably about 12 to about 18 carbon atoms, more desirably stearic acid, together with a polyol, desirably having about 4 to about 8 hydroxys and about 4 to about 8 carbon atoms. Particularly desirable is sorbitol, glycerol, propylene glycol and polyethylene glycol, most desirably sorbitol. Water generally comprises the remainder of the foundation cream. Additionally present can be various emollients such as esters of long chain alkyl carboxylic acids with long chain alkyl alcohols or short chain alkyl alcohols, or esters of short chain alkyl carboxylic acids with long or short chain alkyl alcohols. Long chain is defined as about 10 to 20 carbon atoms, while short chain as about 2 to 8 carbon atoms. Isopropyl palmitate is preferred. Various preservatives, fragrances, chelating agents, emulsifiers and the like can also be present. A small amount of base such as sodium hydroxide or preferably potassium hydroxide can be present and can effect the ease of spreading and tactility of the cream together with the actives.

With respect to the quantities of components appearing in the formulation base, the amount of organic acid is from about 5 to about 20 wt. % of the composition, desirably about 8 to about 16 wt. %. The polyols is from about 0.5 to about 30 wt. % of the composition, desirably about 1 to about 15 wt. % of the composition. The largest component in the composition is water. This is generally from about 60 to about 90 wt. % of the formulation, desirably about 70 to about 85 wt. % of the formulation. The amount of base in the formulation, can vary from about zero to about 1 wt. % of the formulation, preferably from about 0.1 to about 0.8 wt. % of the formulation. At the higher end of the range, for example about 0.7 wt. %, the base particularly potassium hydroxide can effect spreadability of the formulation with or without the presence of emulsifiers.

The quantity of actives can vary significantly as well. With respect to the melanin synthesis inhibitor, there can be from about 0.01 to about 20 wt. % of the composition, desirably about 0.05 to about 10 wt. %. The materials which prevent the skin from further darkening (sunscreens whether organic or inorganic) are from about 0.1 to about 20 wt. % of the composition, desirably from about 0.1 to about 15 wt. % and more desirably about 0.1 to about 5 wt. %. The antioxidant vitamins can vary significantly. Generally, Vitamin E and/or its precursor are present in quantities of from about 0.05 to about 5 wt. % while Vitamins C and A and/or their precursors are presently in reduced quantities such as about 0.001 to about 0.5 wt. % of the composition, desirably from about 0.005 to about 0.04 wt. %.

Emollients can be present and these vary from about 0.5 to about 30 wt. % of the composition, more preferably about 1 to about 15 wt. %. Preservatives, chelating agents, emulsifiers, fragrances and the like are employed at the usual concentrations that achieve their effects.

Preferred active compositions are (a) a combination of Biowhite with OMC and benzophenone-3 with or without at least vitamin or vitamin precursor, (b) combination of Niacinamide, Gatuline with methylene bis benzotriazolyl tetramethyl butyl phenol and OMC with or without at least one vitamin or vitamin precursor, and (c) a combination of vitamin precursor such as SAP, OMC and methylene bis benzotriazolyl tetramethyl butyl phenol and optionally with at least one additional vitamin or vitamin precursor.

Below are examples of the invention.

| Number | Ingredient | 1 | 2 | 3 |
|--------|------------|------|--------|--------|
| 1 | Stearic Acid | 15.0 | 15.0 | 15.0 |
| 2 | Isopropyl Palmitate | 2.0 | 2.0 | 2.0 |
| 3 | PPHB (a) | 0.1 | 0.1 | 0.1 |
| 4 | MPHB (b) | 0.2 | 0.2 | 0.2 |
| 5 | Sorbitol 70% | 3.0 | 3.0 | 3.0 |
| 6 | Potassium Hydroxide | 0.7 | 0.7 | 0.7 |
| 7 | Perfume | 0.6 | 0.6 | 0.6 |
| 8 | Water qs | 76.372 | 75.972 | 76.382 |
| 9 | EDTA | 0.1 | 0.1 | 0.1 |
| 10 | Vitamin A Palmitate | 0.018 | 0.018 | 0.018 |
| 11 | Vitamin E Acetate | 0.1 | 0.1 | 0.1 |
| 12 | SAP (c) | 0.01 | 0.01 | 0.2 |
| 13 | Benzophenone-3 | 0.35 | — | — |
| 14 | OMC (d) | 1.25 | 0.6 | 0.6 |
| 15 | Niacinamide | — | 0.5 | — |
| 16 | Tinosorb M (e) | — | 1.00 | 1.00 |
| 17 | Biowhite (f) | 0.2 | — | — |
| 18 | Gatuline Complex (g) | 0 | 0.1 | — |

(a) Propyl para hydroxybenzoate
(b) Methyl para hydroxybenzoate
(c) Sodium ascorbyl phosphate
(d) Octyl methoxycinnamate
(e) Methylene bis-benzotriazolyl tetramethyl butyl phenol. (Tinosorb M)
(f) Herbal extracts of scutelleria, saxifrage, grape and mulberry
(g) Herbal extracts of aspergillus ferment and licorice.

The compositions of the invention are administered to the skin by rubbing on the skin one to two times a day for a period of 6 to 8 weeks and until a skin lightening effect is observed.

When the cream base formulations of examples 1,2,3 are compared to Fair & Lovely, an Indian lightening cream, all the three base formulations are easier to spread on skin. When the amount of potassium hydroxide in the cream base composition was 0.2 wt. %, with the presence of other emulsifiers the cream base is more sticky and has less skin slip. When there is an absence of KOH and presence of other emulsifiers, the cream base has less skin slip and less gloss.

With respect to skin lightness, the application of Examples 1 and 2 to the skin brings about statistically significant differences in the lightness in the E value (Overall change in skin color) from baseline to 6 weeks readings. A statistically significant difference was also observed in lightness (L value) of skin color between baseline readings and after twice daily application for 6 weeks.

In another study conducted, a statistically significant change was observed in the dE values over control (which was a patch of untreated skin) when Examples 1 and 3 were applied once a day for 61 days.

The Examples had a Sun Protection Factor (SPF) between 4 to 7 versus 3.77 for Fair & Lovely when measured by in vitro methods.

Sun protection factor is used to measure the amount of UV protection offered by the formulation.

What is claimed is:

1. A composition comprising a cream or lotion base, said base further comprising:

a. an active agent or mixture thereof which brings about skin lightening which is an herbal extract complex of scutelleria, saxifrage, grape and mulberry (Biowhite complex); or a mixture of sodium ascorbyl phosphate, niacinamide, and an herbal extract complex of aspergillus ferment and licorice (Gatuline complex); and b. an active agent or mixture thereof which prevents skin from further darkening when exposed to ultraviolet light which is a mixture of octylmethoxycinnamate and benzophenone-3 or a mixture of octylmethoxycinnamate and methylene bis-benzotriazolyl tetramethylbutylphenol.

2. The composition in accordance with claim 1 wherein the base is comprised of about 8 to about 16 wt. % of an alkyl carboxylic acid having about 10 to about 20 carbon atoms and a polyol having about 5 to about 8 hydroxyls and 4 to about 8 carbon atoms.

3. The composition in accordance with claim 2 wherein the acid is stearic acid.

4. The composition in accordance with claim 2 wherein the polyol is sorbitol.

5. The composition in accordance with claim 5 wherein the polyol is sorbitol.

* * * * *